United States Patent
Kerr et al.

(10) Patent No.: US 11,344,508 B2
(45) Date of Patent: May 31, 2022

(54) ANTIMICROBIAL FORMULATIONS FOR THE IMPROVED TREATMENT OF VETERINARY HOOF INFECTIONS

(71) Applicant: Provita Eurotech Ltd, Omagh (GB)

(72) Inventors: Michael Kerr, Tyrone (GB); Teresa Allen, Tyrone (GB)

(73) Assignee: Provita Eurotech Ltd, Omagh (GB)

( * ) Notice: Subject to any disclaimer, the term of this patent is extended or adjusted under 35 U.S.C. 154(b) by 0 days.

(21) Appl. No.: 16/348,337

(22) PCT Filed: Nov. 9, 2017

(86) PCT No.: PCT/GB2017/053382
§ 371 (c)(1),
(2) Date: May 8, 2019

(87) PCT Pub. No.: WO2018/087554
PCT Pub. Date: May 17, 2018

(65) Prior Publication Data
US 2020/0054577 A1 Feb. 20, 2020

(30) Foreign Application Priority Data
Nov. 9, 2016 (GB) ..................................... 1618945

(51) Int. Cl.
| | | |
|---|---|---|
| *A61K 31/115* | (2006.01) | |
| *A61K 33/34* | (2006.01) | |
| *A61K 9/08* | (2006.01) | |
| *A61K 9/107* | (2006.01) | |
| *A61K 47/10* | (2017.01) | |
| *A61K 47/12* | (2006.01) | |
| *A61K 47/44* | (2017.01) | |

(52) U.S. Cl.
CPC ............ *A61K 31/115* (2013.01); *A61K 33/34* (2013.01); *A61K 47/10* (2013.01); *A61K 47/12* (2013.01); *A61K 47/44* (2013.01); *A61K 9/08* (2013.01); *A61K 9/107* (2013.01)

(58) Field of Classification Search
CPC ..................................................... A61K 33/34
See application file for complete search history.

(56) References Cited

U.S. PATENT DOCUMENTS

| | | | |
|---|---|---|---|
| 4,604,283 A | 8/1986 | Gresham | |
| 6,028,104 A | 2/2000 | Schmidt et al. | |
| 6,444,707 B1 | 9/2002 | Lampe et al. | |
| 6,596,325 B1 | 7/2003 | Vroom | |
| 6,683,030 B2 * | 1/2004 | Kober | A01N 25/02 504/313 |
| 6,852,756 B1 | 2/2005 | Ripley et al. | |
| 2009/0110645 A1 | 4/2009 | Morelli et al. | |
| 2010/0233292 A1 | 9/2010 | Rocker et al. | |
| 2013/0129637 A1 | 5/2013 | Beckert et al. | |
| 2014/0287064 A1 | 9/2014 | Swenholt | |
| 2015/0335598 A1 | 11/2015 | Buchalova et al. | |

FOREIGN PATENT DOCUMENTS

| | | |
|---|---|---|
| JP | 2001-509136 A | 7/2001 |
| JP | 2003-514856 A | 4/2003 |
| JP | 2012-510469 A | 5/2012 |
| JP | 2015-512918 A | 4/2015 |
| WO | WO-0223993 A2 | 3/2002 |
| WO | WO-2008031087 A1 | 3/2008 |
| WO | WO-2009053741 A2 | 4/2009 |
| WO | WO-2010062961 A1 | 6/2010 |
| WO | WO-2012024324 A1 | 2/2012 |
| WO | WO-2014098759 | 6/2014 |
| WO | WO-2014134709 A1 | 9/2014 |

OTHER PUBLICATIONS

Durand-Oral, Ilknur, "International Search Report," prepared for PCT/GB2017/053382, dated Jan. 9, 2018, five pages.

* cited by examiner

*Primary Examiner* — Ana Z Muresan
(74) *Attorney, Agent, or Firm* — Winstead PC

(57) ABSTRACT

There is provided a composition comprising an organic material and at least a first surfactant which following addition of an aqueous solution to the composition can form a biphasic system, wherein the biphasic system is useful for the treatment of or prevention of hoof infections. Also provided is a biphasic system useful for the treatment of or prevention of hoof infections, wherein the biphasic system comprises the composition and an aqueous phase wherein the composition is dispersed as droplets within the aqueous phase.

15 Claims, No Drawings

ANTIMICROBIAL FORMULATIONS FOR THE IMPROVED TREATMENT OF VETERINARY HOOF INFECTIONS

FIELD OF THE INVENTION

There are described compositions for use in the treatment of veterinary hoof infections, in particular compositions which can be mixed with aqueous solutions to form biphasic systems for use in footbath treatment regimens.

BACKGROUND

Traditionally the treatment of veterinary hoof infections, including digital dermatitis, is performed using aqueous antimicrobial formulations in a footbath environment. The antimicrobial agents that are commonly used in footbath treatment regimens include aldehydes (notably formaldehyde), copper sulphate and organic acids. This technique has met with both limited clinical success and clinical acceptability, and therefore it is accepted that improvements in the treatment of veterinary hoof infections are required.

SUMMARY OF THE INVENTION

The inventors have determined a number of formulation challenges for the treatment of veterinary hoof infections including limited contact time of an antimicrobial agent with a target site to be treated, limited access of the antimicrobial agent to the target site, and limited retention at the target site.

The inventors consider treatment of veterinary hoof infections using an aqueous biphasic (disperse) system may be advantageous in relation to these challenges.

Accordingly, in a first aspect of the invention there is provided a composition (comprising an organic phase) capable of forming an antimicrobial biphasic system (the product) when mixed with an aqueous solution for use in the treatment of veterinary hoof infections, wherein the composition comprises an organic material and one or more surfactants. In embodiments, in use, when the organic material, for example organic acid ester, fatty acid, or oil, is provided with an aqueous solution, an anti-microbial biphasic system is formed wherein the organic material is dispersed within the aqueous solution.

Suitably the composition may be provided as a single phase (predominately organic phase solution) which becomes biphasic when added to an appropriate quantity of aqueous phase in use. Suitably the organic material may be liquid. As will be understood, it may be advantageous for storage and transport reasons that the composition is provided without being mixed with an aqueous solution or mixed with insufficient aqueous solution such that it does not form a biphasic system until further diluted with aqueous solution. Suitably the composition and product may have a pH of 1 to 3, suitably pH 1 to pH 2.

Suitably, the biphasic system may be provided at temperatures ranging from 0° C. to at least 30° C., suitably 4° C. to 20° C.

In embodiments the composition can further comprise an acid(s) (for example formic or acetic acid), and/or alcohol and/or an antimicrobial agent. Suitably, the organic material which will form the organic phase in a resulting biphasic system may be an oil or an organic acid ester, for example isopropyl myristate.

Suitably, in embodiments, the composition can be provided to form a biphasic phase wherein the dispersed phase is the organic material and the continuous phase is water or another aqueous solution. In embodiments the composition can be mixed with an aqueous solution, for example Hoofsure Endurance™ (Formic Acid 60% to 100%, Acetic Acid 10% to 30% and Ethanol 3% to 7%), a copper solution or a formaldehyde solution as would be known in the art. Suitably, the aqueous solution may comprise an antimicrobial or function as an antimicrobial. In embodiments the composition and a limited amount of aqueous phase may form a solution, rather than a biphasic system. Such a solution can be provided as a concentrate which is then further diluted for example when added to a footbath.

According to a second aspect of the invention there is provided a biphasic system for use in the treatment of veterinary hoof infections comprising a non-aqueous phase, as provided by a composition of the first aspect of the invention, and an aqueous phase, wherein the non-aqueous phase is dispersed as droplets within the aqueous phase. Suitably, a surface-active agent, for example as provided by a composition of the first aspect of the invention, may be provided within the aqueous and/or the non-aqueous phase. Suitably the non-aqueous phase or aqueous phase may contain an antimicrobial agent. In embodiments the aqueous phase can comprise an antimicrobial agent. In embodiments the non-aqueous phase can comprise an antimicrobial agent. In embodiments both phases can comprise an antimicrobial agent, wherein the antimicrobial agent can be the same or different in each phase. As noted above, a biphasic system comprising a non-aqueous and an aqueous phase may suitably be provided as would be understood by those in the art. In embodiments a biphasic system can be provided when the aqueous phase is provided at greater than or equal to 70% with respect to the organic phase as described herein of the system.

In use, the composition (or a solution that is predominantly organic phase, for example when the organic phase is equal to or greater than 30%) is mixed with a large volume of predominantly aqueous solution (for example that can include Hoofsure Endurance™) to form a biphasic system. Suitably, in use, the composition of the first aspect of the invention can be provided with an aqueous solution, wherein the aqueous solution is not provided in sufficient quantity to cause a biphasic system to form (i.e. forms predominately organic phase solution), but when the solution is diluted with water to provide a desired concentration of active ingredient for use to treat an animal, a biphasic system is provided.

As will be appreciated, for ease of transport, a concentrated biphasic system may be provided which can be further diluted on site with water as required.

Alternatively, the composition (or a predominantly organic phase solution) can be packaged separately to an aqueous phase, for example an antimicrobial aqueous phase. The two separate packages can then be mixed as required.

As a further alternative, the composition can be mixed with an aqueous solution to form a predominantly organic phase solution, such that at an insufficient amount of aqueous solution is provided to form a biphasic system. Suitably, according to an aspect of the invention there is provided a kit of parts comprising the composition (or predominantly organic phase solution) and an aqueous solution wherein the composition (or predominantly organic phase solution) and an aqueous solution can be combined, and optionally the kit can comprise a second or further aqueous solution, to allow formation of a biphasic system. In embodiments the kit of parts provides instructions to form the biphasic system. In embodiments the composition (or predominantly organic phase solution) and an aqueous solution can be provided in two separate bottles such that on mixing a suitable ratio of composition to aqueous solution is provided, for example a 1:9 ratio of composition (non-aqueous phase to diluted aqueous phase) to form a biphasic system.

In embodiments the composition when combined with an aqueous solution, for example an antimicrobial aqueous solution, can provide a biphasic system with improved efficacy in killing bacteria. Suitably, the biphasic system may be able to ensure a 100% bacterial kill rate in under 2 minutes, suitably under 1 minute, suitably under 30 seconds.

For example, in embodiments the times for 100% kill of a constant bacterial inoculum can be as follows:

Biphasic system of present invention (3× Minimum Inhibitory Concentration) comprising predominantly organic solution (composition as discussed herein) and an antimicrobial aqueous solution (Hoofsure Endurance™)
  1-2 minutes under clean conditions
  1-2 minutes under dirty conditions
Compared with
Hoofsure Endurance™ (antimicrobial aqueous formulation) (3× Minimum Inhibitory Concentration)
  5 minutes under clean conditions
  5 minutes under dirty conditions
Copper (3× Minimum Inhibitory Concentration)
  >5 minutes under clean conditions
  >5 minutes under dirty conditions
Formaldehyde (3× Minimum Inhibitory Concentration)
  >5 minutes under clean conditions
  >5 minutes under dirty conditions The composition or predominantly organic phase solution may contain antimicrobial agents and may suitably be dispersed as droplets of a preferred size within an aqueous phase that may be antimicrobial. Suitably the preferred size of droplets is in a range of 100 nm to 100 μm, suitably 0.05 μm to 100 μm and optimally between 100 nm to 500 nm, for example 100 to 400 nm.

Without wishing to be bound by theory, it is considered by the inventors that typically, a site of infection, for example the hard and soft surfaces of a hoof, can be hydrophobic. The hydrophobic disperse phase of the present composition or predominately organic phase solution provides for wetting of these surfaces and the wetting is improved when compared to conventional aqueous compositions/formulations. This can provide an enhanced antimicrobial effect.

In particular embodiments the hydrophobic disperse phase can allow improved anti-microbial action within rugae of the hoof wall at the site of infection. Suitably, the hydrophobic disperse phase may remove hydrophobic organic matter and microorganisms from the site of infection.

In embodiments the predominantly organic phase (organic material in the formulation) is liquid at room temperature. In embodiments, the non-aqueous phase (organic material in the composition) can be composed of one or more of the following components:
  Organic acid ester, suitably ethyl ethanoate, benzyl benzoate, isopropyl myristate, capric/caprilic triglycerides;
  Fatty acid, suitably, capric acid, caprylic acid, oleic acid, linolenic acid, linoleic acid;
  Mineral Oil, suitably a paraffin oil;
  Vegetable Oil, for example arachis oil, sunflower oil, rape seed oil, or
  Essential Oil for example tea tree oil, clove oil, peppermint oil, limonene, citronella, sage oil, thyme oil, wintergreen oil.

In embodiments, the organic material of the composition may comprise one, or more than one, of the above components and possess no inherent antimicrobial activity.

In embodiments, the predominantly organic phase can comprise a lipophilic antimicrobial agent. Suitably the lipophilic antimicrobial agent can have a log P>1. Suitably in embodiments the lipophilic antimicrobial agent can be an antimicrobial essential oil.

In embodiments, the aqueous phase of an emulsion (biphasic) of the invention can comprise a pH modifier, for example organic and/or inorganic acid(s), organic and/or inorganic base(s) or, where appropriate, their salts. Suitably a pH modifier may include (but is not limited to), formic acid, acetic acid, sulphuric acid, citric acid, phosphoric acid, sodium hydroxide, potassium hydroxide, triethylamine, triethanolamine or combinations thereof.

Suitably, an aqueous phase can comprise a co-solvent. In embodiments a co-solvent can comprise an alcohol, aprotic solvent (e.g. 2-pyrrolidone, N-methyl pyrrolidone, Dimethylsulphoxide, dimethylformamide, or glycerol formal.

Suitably, the solution comprising the predominately organic phase and/or biphasic system of the invention may comprise a colouring agent.

Suitably an antimicrobial agent in the aqueous phase and optionally the non-aqueous phase may be selected from formaldehyde, copper sulphate, organic acids or combinations thereof.

In embodiments a surface-active agent of the composition or the biphasic system of the invention, either within the aqueous and/or the predominantly organic phase of the emulsion, may include a non-ionic surface-active agent, for example a polyol ester (Span®, Crodamol®), sorbitan(ol) ester ethoxylate (Tween®, Atlas®), alkylaryl polyether alcohol (Triton® X), alkylaryl polyether alcohol (Brij®), fatty acid ethoxylate (Myrj®), ethylene oxide-propylene oxide block copolymer (Pluronic®), alkoxylated cetyl alcohol (Procetyl®), an ionic surface-active agent, for example fatty acid sodium soap, oleine/oleic fatty acid, quaternary ammonium compound, bile salt or the like. Suitably combinations of surface active agent can be provided.

In embodiments a composition of the present invention can be provided in a concentrated form. Suitably, in the biphasic system, the hydrophobic organic phase is presented as the internal phase. In embodiments, this biphasic system can be provided to a footbath solution or diluted in the footbath. The ratio of the volume of biphasic system to the volume of the footbath solution may be chosen to control the antimicrobial efficacy.

Suitably, the predominantly organic phase of the present invention comprises

| Component | Range (w/w) |
| --- | --- |
| First surface active agent (for example Polyoxyethylene (4) lauryl ether) | 5%-45% |
| Denatured Alcohol | 0.1%-15% |
| Formic acid | 0.1%-25% |
| Acetic acid | 0.1%-25% |
| Non-aqueous phase | 0.1%-10% |
| Aqueous phase | 0%-15% |
| Colouring agent | 0%-0.5% |

(This can be considered as the composition with an aqueous solution insufficient to cause a biphasic system to form).

In embodiments, the predominantly organic phase may further comprise at least one of a

| | |
|---|---|
| Second surface-active agent | 2%-15% |
| Third surface-active agent | 0%-15% |

In particular embodiments the predominantly organic phase of the present invention can comprise 5% to 45%, suitably around 38% of Polyethylene glycol dodecyl ether or Polyoxyethylene (4) lauryl ether, for example Brij® L4 (also named Brij 30), 2% to 15%, for example around 10% of a nonionic liquid surfactant, for example Procetyl®, 0.1% to 15%, for example around 8% denatured ethanol, 0.1% to 25%, for example around 6% formic acid, 0.1 to 25%, for example around 16% Acetic acid, 0.1% to 10%, for example around 8% Isopropyl myristate, 0% to 0.5%, for example around 0.2% colouring and 0% to 15% water.

| Component | Range (w/w) |
|---|---|
| Polyoxyethylene (4) lauryl ether or Propylene glycol-5-cethyl alcohol-20 | 5%-45% |
| Non-ionic surfactant | 2%-15% |
| Denatured Alcohol | 0.1%-15% |
| Formic acid | 0.1%-25% |
| Acetic acid | 0.1%-25% |
| Isopropyl myristate | 0.1%-10% |
| Water | 0%-15% |
| Colouring agent | 0%-0.5% |

In particular in embodiments the predominately organic phase of the present invention can comprise 38.8% Brij® L4 (also named Brij 30), 10.4% Procetyl®, 8.3% denatured ethanol, 6.4% formic acid, 16.9% Acetic acid, 8.8% Isopropyl myristate, 0.22% colouring and water.

Suitably a composition or predominately organic phase solution of the invention may be mixed with Hoofsure Endurance™ [Formic acid 60% to 100%, Acetic acid 10% to 30% and ethanol 3% to 7%] at a volume ratio of 0.05:095 to 4:6, and diluted with water to provide final concentration of such embodiment of 0.375% v/v.

Typically Hoofsure Endurance is provided at a concentration such that a dilution rate of 1% v/v is used (0.5 litres makes 50 litres of footbath solution). More concentrated solutions can be provided for topical use. Suitably, when provided in combination with the composition of the present invention, Hoofsure Endurance™ [comprising in the range Formic acid 60% to 100%, Acetic acid 10% to 30% and ethanol 3% to 7%] may be provided at a final concentration of 0.375% v/v.

In embodiments, in the final dilution, the provided components of a composition can be as listed below:

Polyoxyethylene (4) lauryl ether, Propylene glycol-5-cethyl alcohol-20, polysorbate 80, Denatured Alcohol, Formic acid, Acetic acid, Isopropyl myristate, Water, Colouring agent, Benzoic acid, and oil of tea tree.

In particular embodiments a predominately organic phase of the present invention can comprise 5% to 45%, for example around 38% of glycol dodecyl ether or Polyoxyethylene (4) lauryl ether, for example Brij® L4 (also named Brij 30), 2% to 15%, for example around 10% Polyethylene glycol hexadecyl ether, for example Brij® 58, 0.1% to 15%, for example around 8% denatured ethanol, 0.1% to 25%, for example around 6% formic acid, 0.1% to 25%, for example around 16% Acetic acid, 0.1% to 10%, for example around 8% Isopropyl myristate, 0% to 0.5%, for example 0.2% colouring and 0% to 15% water.

In particular embodiments a predominately organic phase of the present invention comprises 38.8% Brij® L4 (also named Brij 30), 10.4% Brij® 58 (Polyethylene glycol hexadecyl ether), 8.3% Denatured ethanol, 6.4% formic acid, 16.9% Acetic acid, 8.8% Isopropyl myristate, 0.22% colouring and water.

This can be diluted with Hoofsure Endurance™ at a volume ratio of 1:9 and diluted with water to provide final concentration of such embodiment of 0.375% v/v. When the mixture is diluted to 0.375%, in the final dilution, the provided components are: Polyoxyethylene (4) lauryl ether, Polyethylene glycol hexadecyl ether, polysorbate 80, Denatured Alcohol, Formic acid, Acetic acid, Isopropyl myristate, Water, Colouring agent, Benzoic acid, and oil of tea tree.

In particular embodiments a predominately organic phase of the present invention can comprise 5% to 45%, for example around 38% Polyethylene glycol dodecyl ether or Polyoxyethylene (4) lauryl, for example Brij® L4 (also named Brij 30), 2% to 15%, for example around 10% Polyethylene glycol hexadecyl ether, for example Procetyl® or Brij® 58, 0.1% to 15%, for example around 8% denatured ethanol, 0.1% to 25%, for example around 6% formic acid, 0.1% to 25%, for example around 16% Acetic acid, 0.1% to 10%, for example around 8% Ethyl ethanoate, 0% to 0.5%, for example around 0.2% colouring and 0% to 15% water.

In particular embodiments a predominately organic phase of the present invention can comprise 38.8% Brij® L4 (also named Brij 30), 10.4% Brij® 58 (Polyethylene glycol hexadecyl ether) or Procetyl®, 8.3% Denatured ethanol, 6.4% formic acid, 16.9% Acetic acid, 8.8% Ethyl ethanoate, 0.22% colouring and water.

In particular embodiments a predominately organic phase of the present invention can comprise 5% to 45%, for example around 38% Polyethylene glycol dodecyl ether or Polyoxyethylene (4) lauryl ether, for example Brij® L4 (also named Brij 30), 2% to 15%, for example around 10% Polyethylene glycol hexadecyl ether, for example Procetyl® or Brij® 58, 0.1% to 15%, for example around 8% denatured ethanol, 0.1% to 25%, for example around 6% formic acid, 0.1 to 25% for example around 16% Acetic acid, 0.1% to 10%, for example around 8% sunflower oil, 0% to 0.5%, for example around 0.2% colouring and 0% to 15% water.

In particular embodiments a predominately organic phase of the present invention can comprise 38.8% Brij® L4 (also named Brij 30), 10.4% Brij® 58 (Polyethylene glycol hexadecyl ether) or Procetyl®, 8.3% Denatured ethanol, 6.4% formic acid, 16.9% Acetic acid, 8.8% sunflower oil, 0.22% colouring and water.

In particular embodiments a predominately organic phase of the present invention can comprise 5% to 45%, for example around 38% Polyethylene glycol dodecyl ether or Polyoxyethylene (4) lauryl ether for example Brij® L4 (also named Brij 30), 2% to 15%, for example around 10% Polyethylene glycol hexadecyl ether, for example Procetyl® or Brij® 58, 0.1% to 15% for example around 8% denatured ethanol, 0.1% to 25%, for example around 6% formic acid, 0.1% to 25%, for example around 16% Acetic acid, 0.1% to 10%, for example around 8% mineral oil, 0% to 0.5%, for example around 0.2% colouring and 0% to 15% water.

In particular a predominately organic phase of the present invention can comprise 38.8% Brij® L4 (also named Brij 30), 10.4% Brij® 58 (Polyethylene glycol hexadecyl ether) or Procetyl®, 8.3% Denatured ethanol, 6.4% formic acid, 16.9% Acetic acid, 8.8% mineral oil, 0.22% colouring and water.

In particular embodiments a predominately organic phase of the present invention can comprise 5% to 45%, for example around 38% Polyethylene glycol dodecyl ether or Polyoxyethylene (4) lauryl ether, for example Brij® L4 (also named Brij 30), 2% to 15%, for example around 10% Polyethylene glycol hexadecyl ether, for example Procetyl® or Brij® 58, 0.1% to 15%, for example around 8% denatured ethanol, 0.1% to 25%, for example around 6% formic acid, 0.1% to 25%, for example around 16% Acetic acid, 0.1% to 10% for example around 8% tea tree oil, 0% to 0.5%, for example around 0.2% colouring and 0% to 15% water.

In particular a predominately organic phase of the present invention can comprise 38.8% Brij® L4 (also named Brij 30), 10.4% Brij® 58 (Polyethylene glycol hexadecyl ether) or Procetyl®, 8.3% Denatured ethanol, 6.4% formic acid, 16.9% Acetic acid, 8.8% tea tree oil, 0.22% colouring and water.

In particular embodiments a predominately organic phase of the present invention can comprise 5% to 45%, for example around 38% Polyethylene glycol dodecyl ether or Polyoxyethylene (4) lauryl ether, for example Brij® L4 (also named Brij 30), 2% to 15%, for example around 10% Polyethylene glycol hexadecyl ether for example Procetyl® or Brij® 58, 0.1% to 15%, for example 8% denatured ethanol, 0.1% to 25%, for example around 6% formic acid, 0.1% to 25% for example around 16% Acetic acid, 0.1% to 10% for example 8% thyme oil, 0% to 0.5%, for example 0.2% colouring and 0% to 15% water.

In particular a predominately organic phase of the present invention can comprise 38.8% Brij® L4 (also named Brij 30), 10.4% Brij® 58 (Polyethylene glycol hexadecyl ether) or Procetyl®, 8.3% Denatured ethanol, 6.4% formic acid, 16.9% Acetic acid, 8.8% thyme oil, 0.22% colouring and water.

In particular embodiments a predominately organic phase of the present invention can comprise 5% to 45% for example around 34% Polyethylene glycol dodecyl ether or Polyoxyethylene (4) lauryl ether, for example Brij® L4 (also named Brij 30), 2% to 15%, for example around 9% Polyethylene glycol hexadecyl ether Procetyl® or Brij® 58, 0% to 15%, for example around 5% Sodium Dodecyl, 0.1% to 15%, for example 8% Denatured ethanol, 0.1% to 25%, for example 6% formic acid, 0.1% to 25%, for example 16% Acetic acid, 0.1% to 10% for example around 8% isopropyl myristate, 0% to 0.5%, for example around 0.2% colouring and 0% to 15% water.

In particular a predominately organic phase solution of the present invention can comprise 34.92% Brij® L4 (also named Brij 30), 9.36% Brij® 58 (Polyethylene glycol hexadecyl ether) or Procetyl®, 4.92 Sodium Dodecyl Sulphate, 8.3% Denatured ethanol, 6.4% formic acid, 16.9% Acetic acid, 8.8% isopropyl myristate, 0.22% colouring and water.

In particular embodiments the a predominately organic phase solution can comprise 5% to 45% for example around 34% Polyethylene glycol dodecyl ether or Polyoxyethylene (4) lauryl ether, for example Brij® L4 (also named Brij 30), 2% to 15%, for example around 9% Polyethylene glycol hexadecyl ether Procetyl® or Brij® 58 (Polyethylene glycol hexadecyl ether), 0% to 15%, for example around 5% Benzalkonium chloride, 0.1% to 15%, for example around 8% denatured ethanol, 0.1% to 25%, for example around 6% formic acid, 0.1% to 25%, for example around 16% Acetic acid, 0.1% to 10% for example around 8% isopropyl myristate, 0% to 0.5% for example 0.2% colouring and 0% to 15% water.

In particular a composition of the present invention can comprise 34.92% Brij® L4 (also named Brij 30), 9.36% Brij® 58 (Polyethylene glycol hexadecyl ether) or Procetyl®, 4.92 Benzalkonium chloride, 8.3% Denatured ethanol, 6.4% formic acid, 16.9% Acetic acid, 8.8% isopropyl myristate, 0.22% colouring and water.

In embodiments a composition of the present invention can be provided as a formulation with another solution for example Hoofsure Endurance™ [Formic Acid 60% to 100%, Acetic Acid 10% to 30% and Ethanol 3% to 7%].

In alternative embodiments, the composition of the present invention can be provided with acidified copper solutions.

Suitably, the composition or predominately organic phase as described herein can be mixed with Hoofsure Endurance™, for example at the ratios

|  | Range v/v |
| --- | --- |
| Composition of present invention | 2%-30% |
| Hoofsure Endurance ™ | 70%-98% |

Suitably mixtures (containing the composition or predominately organic phase and Hoofsure Endurance™) show better bacterial killing properties when the concentration of composition is higher than 0.25%. To enhance the efficiency of the use at least 1% of composition is most suitable.

It has been determined that the tested solutions containing 0.15% (3MIC) copper and 0.125% (MIC) Hoofsure Endurance™ provide a 100% killing time at longer than 5 minutes. When incorporated with 0.02% (or a higher percentage up to 2%) of the emulsions as described herein (10%) the time for complete kill is 5 minutes.

Suitably the composition or predominately organic phase as described herein may be provided such that it can be diluted to 1% of its sold composition.

In embodiments when the composition is added to a footbath solution a stable biphasic system is generated. Suitably the droplet size of the non-aqueous phase can be optimised to enhance the clinical activity of the footbath solution.

According to a third aspect of the present invention there is provided a method of treating a hoof infection comprising the step of providing a composition of the first aspect of the invention or a biphasic system of the second aspect of the invention to an area to be treated on an animal in need thereof.

In embodiments the area to be treated is the rugae of a hoof.

Suitably, a hoof infection may be selected from at least one of papillomatous digital dermatitis (PDD or hairy hoof warts), interdigital dermatitis (stable hoof rot), interdigital phlegmon (hoof rot), laminitis, white line disease and heel erosion.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Preferred features and embodiments of each aspect of the invention are as for each of the other aspects mutatis mutandis unless context demands otherwise.

Examples of the present invention will now be described by way of example only and not as a limitation to the invention described herein or as set out in the attached claims.

EXAMPLES OF FORMULATIONS

Example One

A solution was provided that forms a biphasic system upon addition to a proprietary product (Hoofsure Endurance™ [Formic Acid 60% to 100%, Acetic Acid 10% to 30% and Ethanol 3% to 7%]) and subsequent dilution with water.

The biphasic system showed enhanced antimicrobial activity both under clean and dirty (with the addition of 0.3% Bovine Serum Albumin) against *Escherichia coli* (NCTC12241). The rate of kill assay is based on the British and European standard test conditions BS EN 1276:1997.

In particular a composition or predominately organic phase of the present invention comprising

TABLE 1

| Component | Concentration (% w/w) |
| --- | --- |
| Brij ® L4 (also named Brij 30) | 38.8 |
| Procetyl ® (alkoxylated cetyl alcohol) | 10.4 |
| Denatured ethanol | 8.3 |
| Formic acid | 6.4 |
| Acetic acid | 16.9 |
| Isopropyl myristate | 8.8 |
| Blue liquid colour | 0.22 |
| Water | 10.18 | was mixed with the commercial product Hoofsure Endurance™ at a volume ratio of 1:9 and diluted with water to provide a final concentration of such embodiment of 0.375% v/v.

In the final dilution, the provided components of a composition can be as listed below:

Polyoxyethylene (4) lauryl ether, Propylene glycol-5-cethyl alcohol-20, polysorbate 80, Denatured Alcohol, Formic acid, Acetic acid, Isopropyl myristate, Water, Blue liquid colour, Benzoic acid, and oil of tea tree.

The antimicrobial activity of this mixture, under both clean and dirty conditions (The clean condition doesn't have any bovine albumin in the tested sample, but the dirty condition contains 0.3% bovine albumin) is shown in table 2 below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 2

| | Surviving Bacterial Count (cfu/mL) under clean and dirty conditions | | | | | |
| --- | --- | --- | --- | --- | --- | --- |
| Contact Time (s) | Example 1 Clean[a] | Example 1 Dirty[a] | HSE Clean[b] | HSE Dirty[b] | CS Clean[c] | CS Dirty[c] |
| 0 | $2.8 \times 10^6$ | $1.5 \times 10^6$ | $2.5 \times 10^6$ | $6.5 \times 10^6$ | $3.2 \times 10^6$ | $1.4 \times 10^7$ |
| 30 | $4.5 \times 10^4$ | $3.7 \times 10^4$ | $1.2 \times 10^6$ | $6.5 \times 10^6$ | $1.7 \times 10^6$ | $1.1 \times 10^7$ |
| 60 | 0 | 0 | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Two

A further solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997.

In the solution used in Example 2 Procetyl is replaced with the non-ionic surfactant Brij® 58 (Polyethylene glycol hexadecyl ether).

TABLE 3

| Component | Concentration (% w/w) |
| --- | --- |
| Brij ® L4 (also named Brij 30) | 38.8 |
| Brij ® 58 | 10.4 |
| Denatured ethanol | 8.3 |
| Formic acid | 6.4 |
| Acetic acid | 16.9 |
| Isopropyl myristate | 8.8 |
| Blue liquid colour | 0.22 |
| Water | 10.18 |

The solution (example 2) is mixed with the commercial product Hoofsure Endurance™ (1:9) and diluted with water to provide final concentration of 0.375% v/v.

The antimicrobial activity of this mixture, under both clean and dirty conditions is shown in table 4 below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 4

Surviving Bacterial Count (cfu/mL) under clean and dirty conditions

| Contact Time (s) | Example 2 Clean[a] | Example 2 Dirty[a] | HSE Clean[b] | HSE Dirty[b] | CS Clean[c] | CS Dirty[c] |
|---|---|---|---|---|---|---|
| 0 | $6.8 \times 10^6$ | $6.5 \times 10^6$ | $2.5 \times 10^6$ | $6.5 \times 10^6$ | $3.2 \times 10^6$ | $1.4 \times 10^7$ |
| 30 | $4.2 \times 10^4$ | $1.5 \times 10^4$ | $1.2 \times 10^6$ | $6.5 \times 10^6$ | $1.7 \times 10^6$ | $1.1 \times 10^7$ |
| 60 | 0 | 0 | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Three

A solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example three illustrates the replacement of isopropyl myristate as the organic phase with ethyl ethanoate.

TABLE 5

| Component | Concentration (% w/w) |
|---|---|
| Brij ® L4 (also named Brij 30) | 38.8 |
| Procetyl ® | 10.4 |
| Denatured ethanol | 8.3 |
| Formic acid | 6.4 |
| Acetic acid | 16.9 |
| Ethyl ethanoate | 8.8 |
| Blue liquid colour | 0.22 |
| Water | 10.18 |

The solution (example 3) is mixed with the commercial product Hoofsure Endurance™ (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 6

Surviving Bacterial Count (cfu/mL) under clean and dirty conditions

| Contact Time (s) | Example 3 Clean[a] | Example 3 Dirty[a] | HSE Clean[b] | HSE Dirty[b] | CS Clean[c] | CS Dirty[c] |
|---|---|---|---|---|---|---|
| 0 | $2.8 \times 10^6$ | $1.8 \times 10^6$ | $2.5 \times 10^6$ | $6.5 \times 10^6$ | $3.2 \times 10^6$ | $1.4 \times 10^7$ |
| 30 | $3.7 \times 10^4$ | $2.2 \times 10^5$ | $1.2 \times 10^6$ | $6.5 \times 10^6$ | $1.7 \times 10^6$ | $1.1 \times 10^7$ |
| 60 | 0 | $3.7 \times 10^3$ | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Four

A solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example four illustrates the replacement of isopropyl myristate as the organic phase with sunflower oil.

TABLE 7

| Component | Concentration (% w/w) |
|---|---|
| Brij ® L4 (also named Brij 30) | 38.8 |
| Procetyl ® | 10.4 |
| Denatured ethanol | 8.3 |
| Formic acid | 6.4 |
| Acetic acid | 16.9 |
| Sunflower oil | 0.5 |
| Blue liquid colour | 0.22 |
| Water | 18.48 |

The solution (example 4) is mixed with the commercial product Hoofsure Endurance™ (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 8

Surviving Bacterial Count (cfu/mL) under clean and dirty conditions

| Contact Time (s) | Example 4 Clean[a] | Example 4 Dirty[a] | HSE Clean[b] | HSE Dirty[b] | CS Clean[c] | CS Dirty[c] |
|---|---|---|---|---|---|---|
| 0 | $2.8 \times 10^6$ | $3 \times 10^6$ | $2.5 \times 10^6$ | $6.5 \times 10^6$ | $3.2 \times 10^6$ | $1.4 \times 10^7$ |
| 30 | $8.3 \times 10^3$ | $1.7 \times 10^2$ | $1.2 \times 10^6$ | $6.5 \times 10^6$ | $1.7 \times 10^6$ | $1.1 \times 10^7$ |
| 60 | 0 | 0 | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Five

A solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example five illustrates the replacement of isopropyl myristate as the organic phase with mineral oil.

TABLE 9

| Component | Concentration (% w/w) |
|---|---|
| Brij ® L4 (also named Brij 30) | 38.8 |
| Procetyl ® | 10.4 |
| Denatured ethanol | 8.3 |
| Formic acid | 6.4 |
| Acetic acid | 16.9 |
| Mineral oil | 0.5 |
| Blue liquid colour | 0.22 |
| Water | 18.48 |

The solution (example 5) is mixed with the commercial product Hoofsure Endurance (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 10

Surviving Bacterial Count (cfu/mL) under clean and dirty conditions

| Contact Time (s) | Example 5 Clean[a] | Example 5 Dirty[a] | HSE Clean[b] | HSE Dirty[b] | CS Clean[c] | CS Dirty[c] |
|---|---|---|---|---|---|---|
| 0 | $2.8 \times 10^6$ | $3 \times 10^6$ | $2.5 \times 10^6$ | $6.5 \times 10^6$ | $3.2 \times 10^6$ | $1.4 \times 10^7$ |
| 30 | $1.7 \times 10^4$ | $3 \times 10^3$ | $1.2 \times 10^6$ | $6.5 \times 10^6$ | $1.7 \times 10^6$ | $1.1 \times 10^7$ |
| 60 | 0 | 0 | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Six

A solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example six illustrates the replacement of isopropyl myristate as the organic phase with tea tree oil.

TABLE 11

| Component | Concentration (% w/w) |
|---|---|
| Brij ® L4 (also named Brij 30) | 38.8 |
| Procetyl ® | 10.4 |
| Denatured ethanol | 8.3 |
| Formic acid | 6.4 |
| Acetic acid | 16.9 |
| Tea Tree oil | 0.5 |
| Blue liquid colour | 0.22 |
| Water | 18.48 |

The solution (example 6) is mixed with the commercial product Hoofsure Endurance™ (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 12

Surviving Bacterial Count (cfu/mL) under clean and dirty conditions

| Contact Time (s) | Example 6 Clean[a] | Example 6 Dirty[a] | HSE Clean[b] | HSE Dirty[b] | CS Clean[c] | CS Dirty[c] |
|---|---|---|---|---|---|---|
| 0 | $2.8 \times 10^6$ | $6.8 \times 10^6$ | $2.5 \times 10^6$ | $6.5 \times 10^6$ | $3.2 \times 10^6$ | $1.4 \times 10^7$ |
| 30 | $7.0 \times 10^4$ | $5.3 \times 10^5$ | $1.2 \times 10^6$ | $6.5 \times 10^6$ | $1.7 \times 10^6$ | $1.1 \times 10^7$ |
| 60 | 0 | 0 | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Seven

A solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example seven illustrates the replacement of isopropyl myristate as the organic phase with thyme oil.

TABLE 13

| Component | Concentration (% w/w) |
|---|---|
| Brij ® L4 (also named Brij 30) | 38.8 |
| Procetyl ® | 10.4 |
| Denatured ethanol | 8.3 |
| Formic acid | 6.4 |
| Acetic acid | 16.9 |
| Thyme oil | 0.5 |
| Blue liquid colour | 0.22 |
| Water | 18.48 |

The solution (example 7) is mixed with the commercial product Hoofsure Endurance™ (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 14

Surviving Bacterial Count (cfu/mL) under clean and dirty conditions

| Contact Time (s) | Example 7 Clean[a] | Example 7 Dirty[a] | HSE Clean[b] | HSE Dirty[b] | CS Clean[c] | CS Dirty[c] |
|---|---|---|---|---|---|---|
| 0 | $2.8 \times 10^6$ | $6.5 \times 10^6$ | $2.5 \times 10^6$ | $6.5 \times 10^6$ | $3.2 \times 10^6$ | $1.4 \times 10^7$ |
| 30 | $3.8 \times 10^4$ | $1.8 \times 10^4$ | $1.2 \times 10^6$ | $6.5 \times 10^6$ | $1.7 \times 10^6$ | $1.1 \times 10^7$ |
| 60 | 0 | 0 | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Eight

A solution that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example eight illustrates the replacement of incorporation of the anionic surfactant, sodium dodecyl sulphate, into example one.

TABLE 15

| Component | Concentration (% w/w) |
|---|---|
| Brij ® L4 (also named Brij 30) | 34.92 |
| Procetyl ® | 9.36 |
| Sodium Dodecyl Sulphate | 4.92 |
| Denatured ethanol | 8.3 |
| Formic acid | 6.4 |
| Acetic acid | 16.9 |
| Isopropyl myristate | 8.8 |
| Blue liquid colour | 0.22 |
| Water | 10.18 |

The solution (example 8) is mixed with the commercial product Hoofsure Endurance™ (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 16

| | Surviving Bacterial Count (cfu/mL) under clean and dirty conditions | | | | | |
|---|---|---|---|---|---|---|
| Contact Time (s) | Example 8 Clean[a] | Example 8 Dirty[a] | HSE Clean[b] | HSE Dirty[b] | CS Clean[c] | CS Dirty[c] |
| 0 | $2.8 \times 10^6$ | $1 \times 10^6$ | $2.5 \times 10^6$ | $6.5 \times 10^6$ | $3.2 \times 10^6$ | $1.4 \times 10^7$ |
| 30 | $6 \times 10^4$ | $2.5 \times 10^6$ | $1.2 \times 10^6$ | $6.5 \times 10^6$ | $1.7 \times 10^6$ | $1.1 \times 10^7$ |
| 60 | 0 | $6.2 \times 10^5$ | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Example Nine

A solution was provided that forms a biphasic system upon addition to a proprietary product (Hoofsure Endurance™) and subsequent dilution with water and which shows enhanced antimicrobial activity both antimicrobial activity both under clean and dirty (with the addition of 0.3% Bovine Serum Albumin) against *Escherichia coli* (NCTC12241). The rate of kill assay is based on the British and European standard test conditions BS EN 1276:1997. Example nine illustrates the replacement of incorporation of the cationic surfactant, benzalkonium chloride, into example one.

TABLE 17

| Component | Concentration (% w/w) |
|---|---|
| Brij ® L4 (also named Brij 30) | 34.92 |
| Procetyl ® | 9.36 |
| Benzalkonium chloride | 4.92 |
| Denatured ethanol | 8.3 |
| Formic acid | 6.4 |
| Acetic acid | 16.9 |
| Isopropyl myristate | 8.8 |
| Blue liquid colour | 0.22 |
| Water | 10.18 |

The solution (example 9) is mixed with the commercial product Hoofsure Endurance™ (1:9) and diluted with water to provide final concentration of 0.375% v/v.

The antimicrobial activity of this mixture, under both clean and dirty conditions is shown in the table below. The initial inoculum of microorganism ranged between $10^6$-$10^7$ colony forming units per mL. In addition, the comparative antimicrobial activities of Hoofsure Endurance™ (HSE) solution and copper sulphate (CS) solution, both at concentrations which are three-times their respective minimum inhibitory concentrations are shown.

TABLE 18

| | Surviving Bacterial Count (cfu/mL) under clean and dirty conditions | | | | | |
|---|---|---|---|---|---|---|
| Contact Time (s) | Example 9 Clean[a] | Example 9 Dirty[a] | HSE Clean[b] | HSE Dirty[b] | CS Clean[c] | CS Dirty[c] |
| 0 | $2.8 \times 10^6$ | $1.0 \times 10^6$ | $2.5 \times 10^6$ | $6.5 \times 10^6$ | $3.2 \times 10^6$ | $1.4 \times 10^7$ |
| 30 | $2.0 \times 10^4$ | $4.0 \times 10^6$ | $1.2 \times 10^6$ | $6.5 \times 10^6$ | $1.7 \times 10^6$ | $1.1 \times 10^7$ |
| 60 | 0 | $6.0 \times 10^5$ | $2.3 \times 10^5$ | $3.8 \times 10^6$ | $6.2 \times 10^5$ | $9.7 \times 10^6$ |
| 120 | 0 | 0 | $5.0 \times 10^3$ | $3.2 \times 10^5$ | $3.3 \times 10^5$ | $5.2 \times 10^6$ |
| 300 | 0 | 0 | 0 | 0 | $5.0 \times 10^3$ | $3.2 \times 10^4$ |

[a]The concentration was 0.375% v/v (3x MIC)
[b]The concentration was 0.375% v/v (3x MIC)
[c]The concentration of CS was 0.15% w/v (3x MIC)

Although the invention has been particularly shown and described with reference to particular examples, it will be understood by those skilled in the art that various changes in the form and details may be made therein without departing from the scope of the present invention.

The invention claimed is:
1. A biphasic system comprising:
 a non-aqueous phase comprising:
  an organic material in the form of benzyl benzoate; and
  a surfactant in the form of polyethylene glycol dodecyl ether; and
 an aqueous phase comprising:
  a mixture comprising at least 60% formic acid, 10% to 30% acetic acid, and 3% to 7% ethanol;
 wherein the non-aqueous phase is dispersed as droplets within the aqueous phase and the biphasic system comprises an antimicrobial agent.
2. A composition capable of forming the biphasic system of claim 1 when mixed with an aqueous solution, the composition comprising:
 a. an organic material in the form of benzyl benzoate;
 b. a surfactant in the form of polyethylene glycol dodecyl ether; and
 c. a mixture comprising at least 60% formic acid, 10% to 30% acetic acid, and 3% to 7% ethanol;
 wherein the non-aqueous phase is dispersed as droplets within the aqueous phase and the composition comprises an antimicrobial agent;
 for treatment/prevention of hoof infections.
3. The composition as claimed in claim 2, wherein the composition comprises an
 aqueous solution at less than 90%.
4. The biphasic system as claimed in claim 1 wherein the antimicrobial agent is provided in the aqueous phase.
5. The biphasic system as claimed in claim 1 wherein the antimicrobial agent is provided in the non-aqueous phase.

6. The biphasic system as claimed in claim 1 for use in the treatment of hoof infections.

7. The biphasic system as claimed in claim 1 wherein the non-aqueous phase droplets are of a size 0.05 µm to 100 µm.

8. A kit of parts comprising:
 a. the composition of claim 1; and
 b. an aqueous solution; and
wherein the composition and aqueous solution are capable of being mixed to provide the biphasic system of claim 1.

9. The kit of parts as claimed in claim 8 wherein the composition and aqueous solution are provided in amounts such that when mixed the aqueous solution is provided at 90% or more.

10. The kit of parts as claimed in claim 8, for use in the treatment of hoof infections.

11. A method of treating a hoof infection comprising the step of providing the biphasic system of claim 1 to an area to be treated on an animal in need thereof.

12. The method of claim 11, wherein the area to be treated is the rugae of a hoof.

13. The composition of claim 1 wherein, a hoof infection is selected from at least one of papillomatous digital dermatitis (PDD), interdigital dermatitis (stable hoof rot), interdigital phlegmon (hoof rot), laminitis, white line disease, and heel erosion.

14. The biphasic system of claim 1 wherein, a hoof infection is selected from at least one of papillomatous digital dermatitis (PDD), interdigital dermatitis (stable hoof rot), interdigital phlegmon (hoof rot), laminitis, white line disease, and heel erosion.

15. The method of claim 11 wherein, a hoof infection is selected from at least one of papillomatous digital dermatitis (PDD), interdigital dermatitis (stable hoof rot), interdigital phlegmon (hoof rot), laminitis, white line disease, and heel erosion.

* * * * *